(12) United States Patent
Lehmann, Jr. et al.

(10) Patent No.: US 9,974,569 B2
(45) Date of Patent: May 22, 2018

(54) SPINAL IMPLANT SYSTEM AND METHODS OF USE (71) Applicant: Warsaw Orthopedic, Inc., Warsaw, IN (US)

(72) Inventors: Ronald A. Lehmann, Jr., Englewood, NJ (US); Jason May, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 9 days.

(21) Appl. No.: 14/822,425

(22) Filed: Aug. 10, 2015

(65) Prior Publication Data
US 2017/0042584 A1 Feb. 16, 2017

(51) Int. Cl.
*A61B 17/70* (2006.01)

(52) U.S. Cl.
CPC ...... *A61B 17/7037* (2013.01); *A61B 17/7002* (2013.01); *A61B 17/7032* (2013.01); *A61B 17/7038* (2013.01)

(58) Field of Classification Search
CPC ............ A61B 17/7001; A61B 17/7032; A61B 17/7034; A61B 17/7035; A61B 17/7037; A61B 17/7038; A61B 17/704; A61B 17/7041; A61B 17/7046; A61B 17/84; A61B 17/8605; A61B 17/8685
See application file for complete search history.

(56) References Cited

U.S. PATENT DOCUMENTS

| | | | | |
|---|---|---|---|---|
| 6,540,748 B2* | 4/2003 | Lombardo | ......... | A61B 17/7037 606/264 |
| 6,626,908 B2* | 9/2003 | Cooper | ............. | A61B 17/7032 606/266 |
| 7,766,945 B2* | 8/2010 | Nilsson | ............. | A61B 17/7037 606/266 |
| 8,021,397 B2* | 9/2011 | Farris | ................ | A61B 17/7037 606/266 |
| 8,308,782 B2* | 11/2012 | Jackson | ............ | A61B 17/7008 606/305 |
| 2007/0093826 A1* | 4/2007 | Hawkes | ............. | A61B 17/7032 606/279 |
| 2009/0198280 A1* | 8/2009 | Spratt | ................ | A61B 17/7037 606/267 |
| 2011/0098755 A1* | 4/2011 | Jackson | ............ | A61B 17/7008 606/305 |
| 2011/0106173 A1* | 5/2011 | Lindemann | ........ | A61B 17/7037 606/302 |

(Continued)

FOREIGN PATENT DOCUMENTS

FR 2958531 A1 * 10/2011 ......... A61B 17/7032

OTHER PUBLICATIONS

Translation of FR2958531A1.*

*Primary Examiner* — Lynnsy Summitt (57) ABSTRACT

A bone fastener comprises a first member including an inner surface defining an implant cavity. A part is disposed with the first member and is non-rotatable relative to the inner surface. A second member is disposed at an angle relative to the first member and configured to penetrate tissue. The part axially translates relative to the inner surface and engages the second member to selectively adjust the angle. Implants, systems, constructs, instruments and methods are disclosed.

20 Claims, 3 Drawing Sheets

(56) References Cited

U.S. PATENT DOCUMENTS

| | | | |
|---|---|---|---|
| 2013/0345754 A1* | 12/2013 | Doubler | A61B 17/7037 606/266 |
| 2016/0113684 A1* | 4/2016 | Rezach | A61B 17/7032 606/278 |
| 2016/0262801 A1* | 9/2016 | Rezach | A61B 17/7032 |

* cited by examiner

SPINAL IMPLANT SYSTEM AND METHODS OF USE

TECHNICAL FIELD

The present disclosure generally relates to medical devices for the treatment of spinal disorders, and more particularly to a surgical implant system including a bone fastener.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener comprises a first member including an inner surface defining an implant cavity. A part is disposed with the first member and is non-rotatable relative to the inner surface. A second member is disposed at an angle relative to the first member and configured to penetrate tissue. The part axially translates relative to the inner surface and engages the second member to selectively adjust the angle. In some embodiments, systems, implants, constructs, instruments and methods are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a spinal implant system including a bone fastener. In one embodiment, the spinal implant system includes an implant comprising an adjustable bone screw that is employed with a method for manipulating a spine.

In some embodiments, the spinal implant system comprises an adjusting screw for spinal manipulation. In some embodiments, the spinal implant system comprises a spinal implant, such as, for example, a bone screw, having a shaft and a receiver that can be utilized as a multi-axial or uniaxial screw. In some embodiments, the bone screw is configured for adjusting the shaft-receiver angle while tightening a closure mechanism, such as, for example, a setscrew. In some embodiments, the adjustment of the bone screw facilitates use in deformity correction procedures. In some embodiments, the shaft can be locked at various angles relative to the receiver.

In some embodiments, the spinal implant system includes a bone screw configured to form a differential angle to allow the screw shaft to be disposed in a flat configuration as a set screw engages a receiver. In some embodiments, the receiver includes an opening configured for disposal of a post. In some embodiments, the post is configured to engage a flat head of a screw shaft. In some embodiments, the screw shaft rotates to a zero angle position as the set screw is engaged with the receiver. In some embodiments, the set screw is configured to lock the screw shaft at various angles to prevent the bone screw from plowing into a spinal canal.

In some embodiments, the spinal implant system comprises a bone fastener including a tulip head, a crown assembly, a retaining ring and a bone screw shaft. In some embodiments, the crown assembly includes a crown having a protrusion, such as, for example, a spherical protrusion configured to engage a top surface of the bone screw shaft to force bone screw rotation relative to the tulip head. In some embodiments, the spinal implant system is configured to selectively lock a spinal rod and bone screw in an angular orientation. In some embodiments, the spinal implant system is configured to selectively lock a spinal rod and bone screw in an angular orientation in a single step. In some embodiments, the bone screw shaft is configured to lock at an angle relative to the tulip head. In some embodiments, the bone screw shaft is configured to lock at an angle relative to the spinal rod. In some embodiments, the spinal implant system is configured to facilitate correction of spinal rotation for scoliosis in an axial plane. In some embodiments, the spinal implant system is configured to facilitate increasing lordosis or kyphosis in a sagittal plane.

In some embodiments, the spinal implant system is employed with a method for treating a spine, which includes the steps of disposing a bone screw shaft at a large initial angle with respect to the tulip head. In some embodiments, the method includes the step of forcing a crown down onto the bone screw shaft and rotating the bone screw shaft. In some embodiments, the method includes the step of decreasing the final screw angle such that the bone screw shaft is fully aligned with the tulip head.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 1:
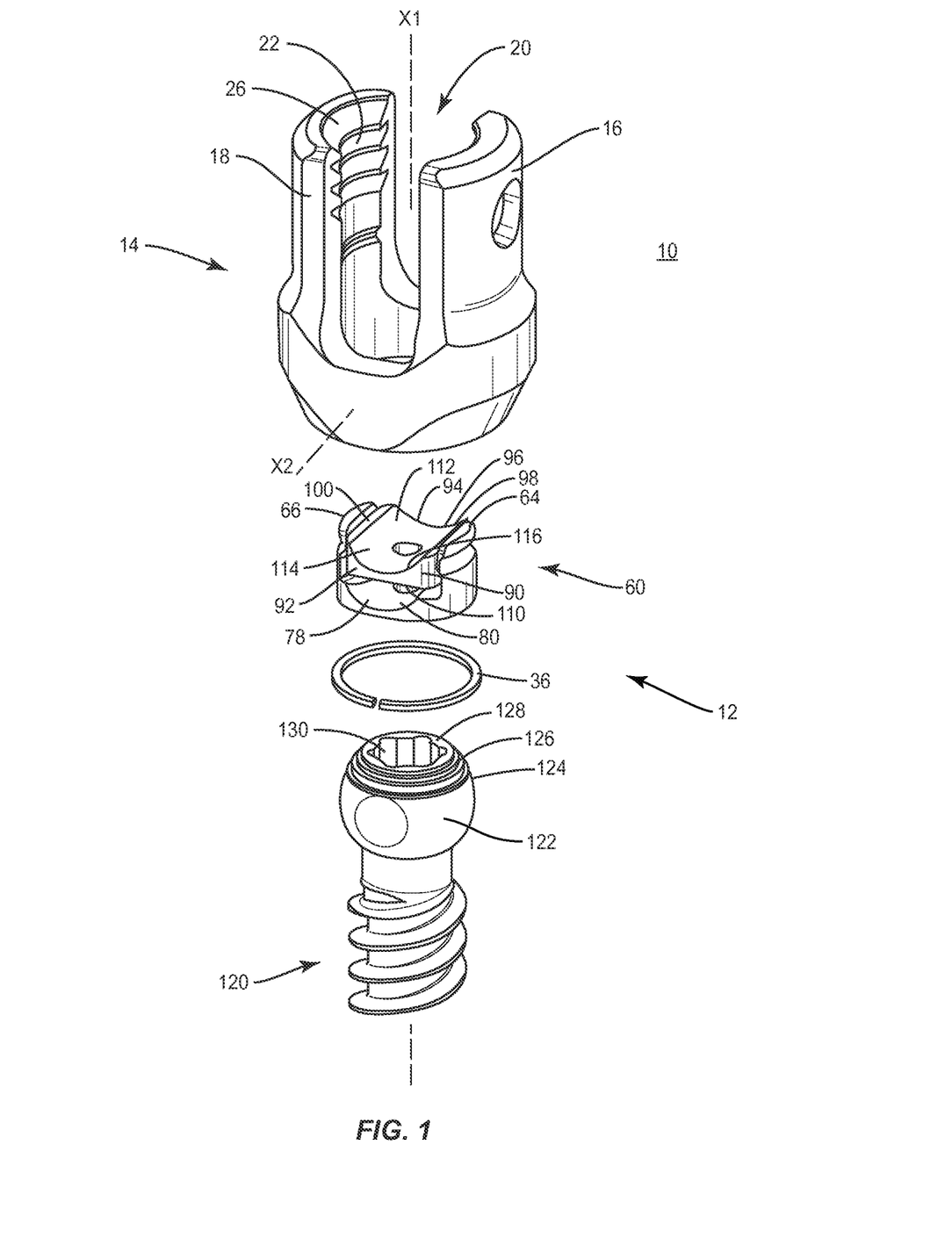
FIG. 1 is a break away, perspective view of components of one embodiment of a spinal implant system in accordance with the principles of the present disclosure with parts separated.

In some embodiments, spinal implant system 10 comprises a bone fastener, such as, for example, a bone screw 12 that includes a member, such as, for example, a receiver 14 connected with a member, such as, for example, a shaft 120. Receiver 14 extends along and defines an axis X1, as shown in FIG. 1. Receiver 14 includes a pair of spaced apart arms 16, 18 that define an implant cavity 20 therebetween configured for disposal of a component of a spinal construct, such as, for example, a spinal rod 142.

Arms 16, 18 each extend parallel to axis X1. In some embodiments, arm 16 and/or arm 18 may be disposed at alternate orientations, relative to axis X1, such as, for example, transverse, perpendicular and/or other angular orientations such as acute or obtuse, coaxial and/or may be offset or staggered. Arms 16, 18 each include an arcuate outer surface extending between a pair of side surfaces. At least one of the outer surfaces and the side surfaces of arms 16, 18 have at least one recess or cavity therein configured to receive an insertion tool, compression instrument and/or instruments for inserting and tensioning bone screw 12. In some embodiments, arms 16, 18 are connected at proximal and distal ends thereof such that receiver 14 defines a closed spinal rod slot.

Cavity 20 is substantially U-shaped. In some embodiments, all or only a portion of cavity 20 may have alternate cross section configurations, such as, for example, closed, V-shaped, W-shaped, oval, oblong, triangular, square, polygonal, irregular, uniform, non-uniform, offset, staggered, and/or tapered. Receiver 14 includes a surface, such as, for example, a wall 22. A portion of wall 22 includes a thread form 24 located adjacent arm 16 and a thread form 26 located adjacent arm 18. Thread forms 24, 26 are each configured for engagement with a coupling member, such as, for example, a setscrew 140, to retain a spinal construct, such as, for example, a spinal rod 142 within cavity 20. In some embodiments, wall 22 may be disposed with the coupling member in alternate fixation configurations, such as, for example, friction fit, pressure fit, locking protrusion/recess, locking keyway and/or adhesive. In some embodiments, all or only a portion of wall 22 may have alternate surface configurations to enhance engagement with a spinal rod and/or a setscrew, such as, for example, rough, arcuate, undulating, mesh, porous, semi-porous, dimpled and/or textured. In some embodiments, receiver 14 may include alternate configurations, such as, for example, closed, open and/or side access.

Figure 2:
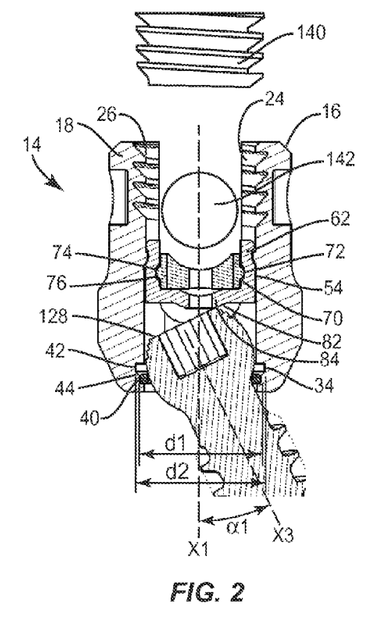
FIG. 2 is a cross section view of the components shown in FIG. 1.

Wall 22 defines a cavity, such as, for example, a groove 34 configured for disposal of an element, such as, for example, a circumferential ring 36. Ring 36 includes a circumference that extends between ends defining an opening, such as, for example, a gap, which facilitates expansion and contraction. Groove 34 includes a portion, such as for, example, a circumferential channel 40 having a diameter d1 and a portion, such as for, example, a circumferential channel 42 having a diameter d2, as shown in FIG. 2. In some embodiments, diameter d2 is greater than diameter d1.

Channel 42 is disposed adjacent and proximal to channel 40. Channel 42 is separated from channel 40 by a protrusion, such as, for example, a lip 44. In some embodiments, shaft 120 is manually engageable with receiver 14 and/or shaft 120 is coupled with receiver 14 in a non-instrumented assembly such that ring 36 translates from and into channels 40, 42, and over lip 44. In some embodiments, ring 36 is expandable and resilient between a contracted and/or capture orientation, as shown for example in FIGS. 2-5 and an expanded orientation (not shown) for assembly of shaft 120 with receiver 14.

Wall 22 includes a cavity, such as, for example, a slot 54 configured to receive a flange of a part, such as, for example, a crown 60, as discussed herein. Wall 22 includes an inner profile that defines a perimeter of cavity 20. Crown 60 is configured for disposal within the inner profile of wall 22 and/or the perimeter of cavity 20 of receiver 14. Crown 60 includes an outer profile and/or perimeter that fits within the inner profile of wall 22. An outer surface of crown 60 engages wall 22. In some embodiments, crown 60 engages wall 22 such that crown 60 is fixed in rotation with wall 22 and/or non-rotatable about axis X1. In some embodiments, crown 60 engages wall 22 such that crown 60 is fixed in rotation with wall 22 and/or non-rotatable about axis X1, and translatable within slot 54 such that crown 60 is translatable relative to wall 22 and along axis X1. In some embodiments, this configuration facilitates translation of crown 60 within slot 54, which facilitates positioning of a head 122 with receiver 14 so that head 122 can be locked with receiver 14, as described herein.

Crown 60 includes a wall 62 defining an extension, such as, for example, an arm 64 and an extension, such as, for example, an arm 66. In some embodiments, arms 64, 66, are keyed to a portion of wall 22 defining slot 54. In some embodiments, arms 64, 66 engage wall 22 such that crown 60 is fixed in rotation with wall 22 and/or non-rotatable about axis X1. In some embodiments, arms 64, 66 engage wall 22 such that crown 60 is fixed in rotation with wall 22 and/or non-rotatable about axis X1, and arms 64, 66 are translatable within slot 54 such that crown 60 is translatable relative to wall 22 and along axis X1.

Arms 64, 66 are configured to support relative movement of a part, such as, for example, a saddle 90. In some embodiments, crown 60 and saddle 90 comprise a crown assembly of bone screw 12. Wall 62 includes a surface 70 that defines a track 72 adjacent arm 64. Wall 62 includes a surface 74 that defines a track 76 adjacent arm 66. Tracks 72, 76 are configured to facilitate translation of saddle 90 relative to crown 60, as described herein. Arms 64, 66 are configured to guide saddle 90 along tracks 72, 76 relative to crown 60. Wall 62 includes a surface 78 that defines an arcuate portion 80 configured for disposal of at least a portion of an implant, such as, for example, a spinal rod (not shown), which may be positioned with bone screw 12 and/or vertebral tissue.

Crown 60 includes a surface 82 that defines an arcuate portion, such as, for example, a protrusion 84. Protrusion 84 is configured to engaged shaft 120 for selective adjustment of an angle of an axis X3 of shaft 120 relative to axis X1 of receiver 14. In some embodiments, protrusion 84 has a spherical configuration. In some embodiments, all or only a portion of protrusion 84 may have alternate cross section configurations, such as, for example, V-shaped, W-shaped, oval, oblong, triangular, square, polygonal, irregular, uniform, non-uniform, offset, staggered, and/or tapered.

Figure 5:
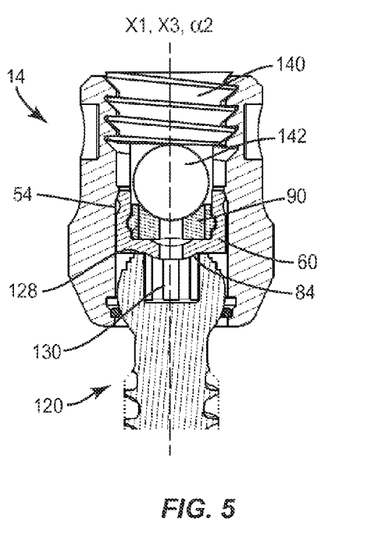
FIG. 5 is a cross section view of the components shown in FIG. 1.

Shaft 120 is disposed in a first orientation, as shown in FIG. 2, and disposed such that axis X3 is disposed at angle α1 relative to axis X1. In some embodiments, axis X3 is disposed at angle α1 relative to axis X1 such that shaft 120 is disposed in non-alignment or out of alignment with receiver 14. Crown 60 is configured to translate, in a direction shown by arrow A in FIG. 3, relative to receiver 14 causing protrusion 84 to engage a surface 128 of head 122 to apply a force, as shown by arrow B in FIG. 3, to surface 128 of shaft 120. The arcuate surface of protrusion 84 slidably engages surface 128 and/or the inner surface defining socket 130 to rotate shaft 120, in a direction shown by arrow C in FIG. 4, between the first orientation and a second orientation, as shown in FIG. 5, such that shaft 120 is disposed at angle α2 relative to axis X1. In some embodiments, in the second orientation, angle α2 is equal to 0 degrees such that shaft 120 is disposed co-axial with axis X1, as shown in FIG. 5, and protrusion 84 is disposed with socket 130. In some embodiments, angle α2 is in a range of 0 to 30 degrees and can be positioned and locked at various angles relative to axis X1. In some embodiments, axis X3 is disposed at angle α2 relative to axis X1 such that shaft 120 is disposed in alignment with receiver 14. Engagement of protrusion 84 with shaft 120 is configured to lock shaft 120 with receiver 14 to prevent and/or resist rotation of shaft 120 relative to receiver 14.

Saddle 90 extends between an end 92 and an end 94. Saddle 90 includes a surface 96 defining a wall 98 and a wall 100. Walls 98, 100 are configured to fit within the outer profile and/or perimeter of crown 60. In some embodiments, saddle 90 fits within the outer profile and/or perimeter of crown 60 such that the sub-assembly of crown 60/saddle 90 is disposed, such as, for example, inserted and/or loaded upwardly through a lower opening of receiver 14 that communicates with cavity 20 to fit within the inner profile of wall 22.

Wall 98 includes a surface 102 that defines a protrusion 104 configured for moveable disposal within track 72, as described herein. Wall 100 includes a surface 106 that defines a protrusion 108 configured for moveable disposal within track 76, as described herein. In some embodiments, this configuration allows saddle 90 to rotate relative to crown 60 in a plane, such as, for example, a sagittal plane of a body and/or vertebrae.

Saddle 90 includes a surface 110 and a surface 112. Surface 110 extends between ends 92, 94 and is configured for slidable engagement with surface 78 of crown 60 along an arcuate pathway of the components. Surface 112 is configured to engage at least a portion of an implant, such as, for example, a spinal rod (not shown) and is moveable relative to crown 60 in a plane, such as, for example, a sagittal plane of a body and/or vertebrae. Surface 112 defines a concave surface 114 that defines an implant cavity 116.

In some embodiments, receiver 14 defines an axis X2 oriented transverse to axis X1. Saddle 90 is configured to receive and movably support spinal rod 142 such that spinal rod 142 can translate axially, rotate and/or pivot relative to receiver 14 along and about axis X2 prior to fixation with saddle 90. In some embodiments, spinal rod 142 may be disposed within cavity 20 for relative movement in orientations relative to axis X2, such as, for example, transverse, perpendicular and/or other angular orientations such as acute or obtuse, co-axial and/or may be offset or staggered. In some embodiments, axis X2 may be disposed at angular orientations relative to axis X1, such as, for example, acute or obtuse.

In some embodiments, saddle 90 may be elastic and pliable in a configuration to react to forces applied and/or force changes, such as, for example, positioning treatment, patient growth, trauma and degeneration, and/or component creep, deformation, damage and degeneration, to maintain the applied force transmitted from an implant positioned in cavity 20 substantially constant. In some embodiments, saddle 90 can facilitate maintenance of a holding force on an implant positioned in cavity 20 to retain the holding force relatively constant despite growth and changes.

Shaft 120 is configured to penetrate tissue, such as, for example, bone. Head 122 includes a substantially spherical proximal portion configured for moveable disposal with receiver 14 and crown 60. Head 122 includes a surface 124 that defines a plurality of ridges 126 to improve purchase of head 122 with crown 60. Head includes a surface 128 that is substantially flat. Protrusion 84 is configured to engage surface 128 of head 122 to cause shaft 120 to rotate facilitating selective adjustment of the angle of axis X3 of shaft 120 relative to axis X1 of receiver 14. In some embodiments, this configuration allows shaft 120 to be rotatable relative to axis X1 through a single plane, such as, for example, a transverse plane.

In some embodiments, a socket 130 includes a hexalobe geometry configured for disposal of a similarly shaped bit of a tool, such as, for example, a driver (not shown) to engage the driver with head 122 to rotate shaft 120. Socket 130 is in communication with cavity 20 such that a driver may be inserted between arms 16, 18 and translated axially, until the bit of the driver is disposed in socket 130. In some embodiments, socket 130 has a cruciform, phillips, square, hexagonal, polygonal, star cross sectional configuration configured for disposal of a correspondingly shaped portion of a driver.

In some embodiments, spinal implant system 10 comprises a spinal implant kit, which includes a plurality of members, such as, for example, implant receivers 14. Receiver 14 is configured for selection from the implant receivers 14 such that receiver 14 is connectable with an interchangeable member, such as, for example, shaft 120. In some embodiments, receiver 14 is configured for selection from the implant receivers 14 such that receiver 14 is connectable with a compatible shaft 120.

In some embodiments, an interchangeable mating element, such as, for example, a head 122 of shaft 120 is interchangeable with a mating element, as described herein, of each of the implant receivers 14 to form a selected bone screw 12 having a selected movement of its component parts and/or movement relative to tissue. In some embodiments, the selected movement includes rotation and/or pivotal movement of shaft 120 relative to receiver 14 about one or a plurality of axes. In some embodiments, the selected movement includes rotation and/or pivotal movement of shaft 120 relative to receiver 14 through one or a plurality of planes. In some embodiments, shaft 120 is connected to a selected receiver 14 to comprise a multi-axial fastener. In some embodiments, shaft 120 is connected to a selected receiver 14 to comprise a uniaxial fastener. In some embodiments, spinal implant system 10 comprises a spinal implant kit, which includes receivers 14 and alternate receivers, such as those described herein.

In assembly, operation and use, spinal implant system 10, similar to the systems and methods described herein, includes bone screw 12 described herein, a coupling member, such as, for example, a set screw 140 and an implant, such as, for example, a spinal rod 142. The components of spinal implant system 10 are employed with a surgical procedure for treatment of a spinal disorder affecting a section of a spine (not shown) of a patient, as discussed herein. Spinal implant system 10 is employed with a surgical procedure for treatment of a condition or injury of an affected section of the spine. One or more bone screws 12 and one or a plurality of spinal implants, such as, for example, vertebral rods can be delivered or implanted as a pre-assembled device or can be assembled in situ. The components of spinal implant system 10 may be may be completely or partially revised, removed or replaced.

In some embodiments, a receiver 14 is selected for assembly with shaft 120 such that one or more bone screws 12 have a selected movement of its component parts and/or movement relative to tissue, with crown 60 and saddle 90 disposed therein. In some embodiments, receiver 14 is engaged with head 122 causing ring 36 to translate, expand and engage groove 34 of receiver 14 such that head 122 translates through ring 36 and is assembled with receiver 14. In some embodiments, head 122 may be assembled with receiver 14 and ring 36 may be assembled with groove 34. In some embodiments, receiver 14 is attached with shaft 120 such that receiver 14 is selectively and rotatable relative to shaft 120 within a transverse plane of vertebrae.

In some embodiments, shaft 120 is threaded and engaged with tissue, such as, for example, vertebrae. In some embodiments, bone screw 12 is disposed adjacent vertebrae at a surgical site and is manipulated to drive, torque, insert or otherwise connect bone screw 12 with vertebrae.

Shaft 120 is disposed in the first orientation, as shown in FIG. 2, such that axis X3 is disposed at angle α1 relative to axis X1. In some embodiments, saddle 90 is selectively translatable along tracks 72, 76 relative to crown 60 in the sagittal plane to accommodate sagittal anatomical differences. Saddle 90 receives and movably supports spinal rod 142 such that spinal rod 142 is movable within cavity 20, as described herein. In some embodiments, this configuration provides movement of saddle 90 to facilitate sagittal accommodation of spinal rod 142 such that bone screw 12 provides angular accommodation in a transverse plane and a sagittal plane of vertebrae.

Figure 3:
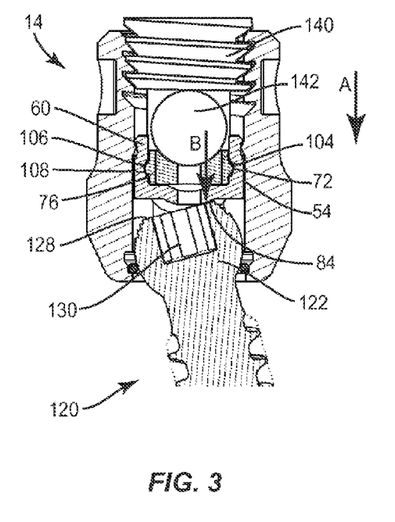
FIG. 3 is a cross section view of the components shown in FIG. 1.
Figure 4:
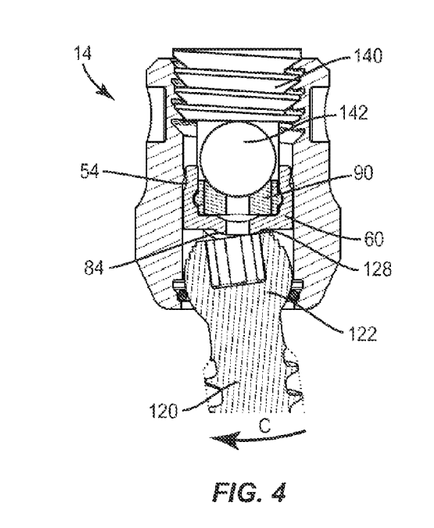
FIG. 4 is a cross section view of the components shown in FIG. 1.

Spinal rod 142 is disposed with receiver 14 and set screw 140 is engaged with receiver 14 and spinal rod 142, as shown in FIG. 3. As set screw 140 is translated into engagement with spinal rod 142, spinal rod 142 applies a force to saddle 90 and crown 60. Shaft 120 is disposed in a first orientation, as shown in FIG. 2, and disposed such that axis X3 is disposed at angle α1 relative to axis X1.

Crown 60 translates, in a direction shown by arrow A in FIG. 3, relative to receiver 14 causing protrusion 84 to engage surface 128 of head 122 to apply a force, as shown by arrow B in FIG. 3, to surface 128. The arcuate surface of protrusion 84 slidably engages surface 128 and/or the inner surface defining socket 130 to rotate shaft 120, in a direction shown by arrow C in FIG. 4, between the first orientation and the second orientation, as shown in FIG. 5, such that shaft 120 is disposed at angle α2 relative to axis X1.

In some embodiments, protrusion 84 slidably engages shaft 120, as described herein, to relatively manipulate, translate and/or rotate spinal rod 142, receiver 14 and/or shaft 120, such that one or a plurality of forces and/or moments are applied to vertebrae to create, for example, a derotation force for a spinal treatment. In some embodiments, such forces may be employed to displace, pull, twist or align vertebrae. In some embodiments, such forces may be employed to correct spinal rotation for scoliosis in an axial plane. In some embodiments, such forces may be employed to increase lordosis or kyphosis in a sagittal plane.

In some embodiments, protrusion 84 slidably engages shaft 120, as described herein, to relatively manipulate, translate and/or rotate spinal rod 142, receiver 14 and/or shaft 120, such that spinal rod 142 is locked with bone screw 12 in a single step. In some embodiments, protrusion 84 slidably engages shaft 120, as described herein, to relatively manipulate, translate and/or rotate spinal rod 142, receiver 14 and/or shaft 120, such that an angle of shaft 120 can be locked relative to receiver 14 and spinal rod 142 individually.

In the second orientation, angle α2 is equal to 0 degrees such that shaft 120 is disposed co-axial with axis X1 and protrusion 84 is disposed with socket 130. Engagement of set screw 140 with spinal rod 142 and protrusion 84 is engaged with surface 128 to lock shaft 120 with receiver 14 to prevent and/or resist rotation of shaft 120 relative to receiver 14.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments the agent may be a hydroxyapatite coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone screws 12 such as those described herein and/or fixation elements, which may be employed with a single vertebral level or a plurality of vertebral levels. In some embodiments, bone screws 12 may be engaged with vertebrae in various orientations, such as, for example, series, parallel, offset, staggered and/or alternate vertebral levels. In some embodiments, bone screws 12 may be configured as multi-axial screws, sagittal angulation screws, pedicle screws, mono-axial screws, uni-planar screws, fixed screws, anchors, tissue penetrating screws, conventional screws, and/or expanding screws. In some embodiments, bone screws 12 may be employed with wedges, anchors, buttons, clips, snaps, friction fittings, compressive fittings, expanding rivets, staples, nails, adhesives, posts, connectors, fixation plates and/or posts.

Figure 6:
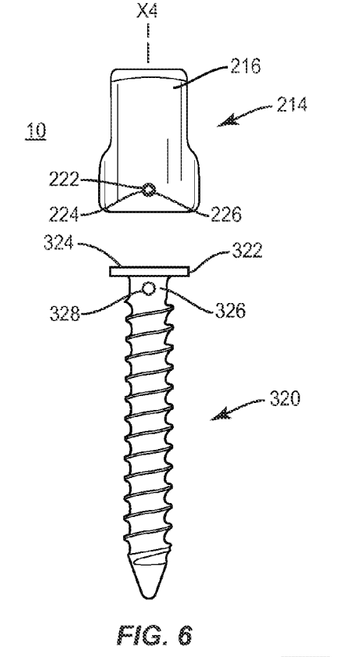
FIG. 6 is a perspective view of components of one embodiment of a spinal implant system in accordance with the principles of the present disclosure with parts separated.
Figure 7:
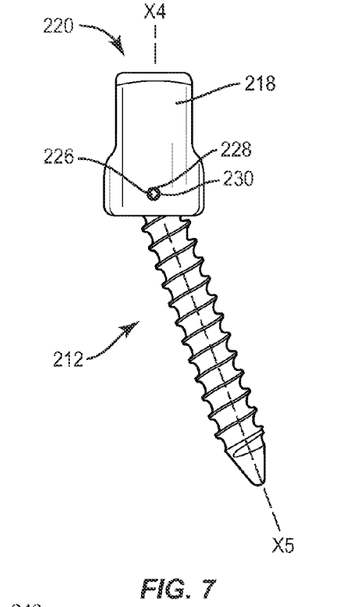
FIG. 7 is a side view of components of one embodiment of a spinal implant system in accordance with the principles of the present disclosure.
Figure 8:
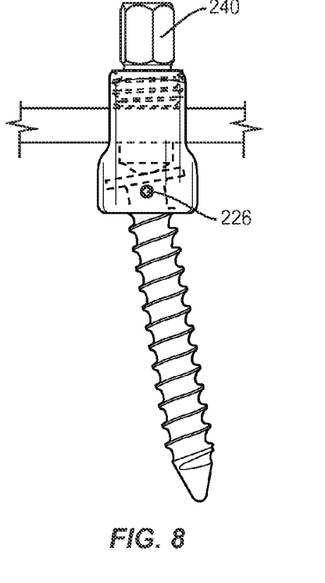
FIG. 8 is a side view of components of one embodiment of a spinal implant system in accordance with the principles of the present disclosure.
Figure 9:
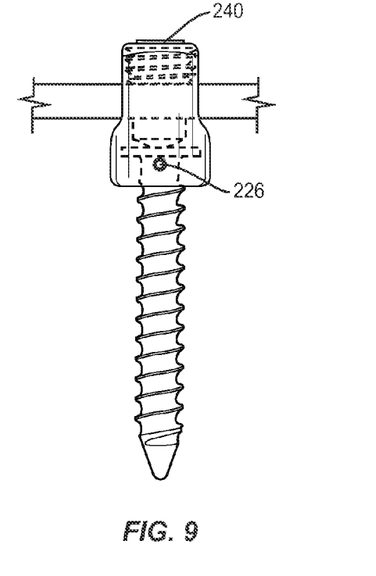
FIG. 9 is a side view of the components shown in FIG. 8.

In one embodiment, as shown in FIGS. 6-9, spinal implant system 10, similar to the systems and methods described herein, includes a bone screw 212, similar to bone screw 12 described herein, having receiver 214, similar to receiver 14 described herein. Receiver 214 includes crown 60 and saddle 90 described herein, and is connectable with shaft 320, similar to shaft 120 described herein. Receiver 214 extends along and defines an axis X4, as shown in FIG. 6. Receiver 214 includes a pair of spaced apart arms 216, 218 that define an implant cavity 220 therebetween configured for disposal of a component of a spinal construct, such as, for example, a spinal rod (not shown). Arm 216 includes a surface 222 that defines an opening 224. Opening 224 is configured for disposal of a pin 226. Arm 218 includes a surface 228 that defines an opening 230. Opening 230 is configured for disposal of pin 226. Pin 226 is configured to rotatably connect shaft 320 with receiver 214.

Shaft 320 is configured to penetrate tissue, such as, for example, bone. A head 322 includes a substantially flat surface 324 configured for moveable disposal with receiver 214, crown 60 and saddle 90. Shaft 320 includes a surface 326 that defines an opening 328. Opening 328 is configured for disposal of pin 226. A set screw 240 and a spinal rod are configured to translate saddle 90 and crown 60 such that protrusion 84, as described herein, engages surface 324 of head 322 to cause shaft 320 to rotate facilitating selective adjustment of an angle of axis X5 of shaft 320 relative to axis X4 of receiver 214, similar to the systems and methods described herein, to relatively manipulate, translate and/or rotate the components of bone screw 212, similar to that described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
   a first member including an inner surface defining a groove and spaced apart arms that define an implant cavity therebetween;
   a part disposed with the first member and being non-rotatable relative to the inner surface;
   a second member being disposed at an angle relative to the first member and configured to penetrate tissue;
   a ring disposed in the groove such that a head of the second member extends through the ring to prevent downward axial translation of the second member relative to the first member; and
   a spinal rod disposable with the implant cavity,
   wherein the part axially translates relative to the inner surface and engages the second member to selectively adjust the angle, and
   wherein the part includes a crown that is non-rotatable relative to the inner surface and a saddle that is movable relative to the crown, the crown comprising a spherical protrusion engageable with the second member to selectively adjust the angle.

2. A bone fastener as recited in claim 1 wherein the crown includes an even distal surface including the spherical protrusion projecting therefrom.

3. A bone fastener as recited in claim 1, wherein the part engages the second member to rotate the second member between a first orientation such that the second member is disposed at a first angle relative to the first member and a second orientation such that the second member is disposed at a second angle relative to the first member.

4. A bone fastener as recited in claim 3, wherein the first member defines a longitudinal axis and in the second orientation the second angle is disposed relative to the longitudinal axis and the second angle is zero.

5. A bone fastener as recited in claim 3, wherein in the second orientation the second member is locked with the first member.

6. A bone fastener as recited in claim 1, wherein the part engages the second member to rotate the second member between a first orientation such that the second member is disposed in non-alignment with the first member and a second orientation such that the second member is disposed in alignment with the first member.

7. A bone fastener as recited in claim 6, wherein the first member defines a longitudinal axis and in the second orientation the second member is co-axially aligned with the longitudinal axis.

8. A bone fastener as recited in claim 1, wherein the second member includes a proximal end having an even surface engageable with the part.

9. A bone fastener as recited in claim 1, wherein the crown includes a pair of arms that support relative movement of the saddle.

10. A bone fastener as recited in claim 1, wherein the crown comprises a pair of arms, the arms of the crown each having a track, the saddle comprising a pair of protrusions, the protrusions each being movably disposed within one of the tracks to facilitate movement of the saddle relative to the crown.

11. A bone fastener as recited in claim 1, wherein the saddle is selectively rotatable to an angular orientation in a range of approximately 0 to 30 degrees relative to the first member within a plane of a body.

12. A bone fastener as recited in claim 1, wherein the groove comprises a first channel and a second channel that is separated from the first channel by a lip, the first channel having a diameter that is greater than that of the second channel.

13. A bone fastener as recited in claim 1, wherein the crown includes tracks and arms that are configured to guide the saddle along the tracks relative to the crown.

14. A bone fastener as recited in claim 13, wherein the saddle comprises a pair of protrusions, the protrusions each being movably disposed within one of the tracks.

15. A bone fastener as recited in claim 1, wherein the crown includes an arcuate portion configured for disposal of a portion of the spinal rod.

16. A spinal implant system comprising:
    a receiver including an inner surface defining an implant cavity;
    a crown being non-rotatable relative to the inner surface and a saddle movable relative to the crown;
    a bone screw shaft disposed at an angle relative to the receiver and including a head; and
    a spinal rod disposable with the implant cavity,
    wherein the crown axially translates relative to the inner surface and engages the head to selectively adjust the angle, the crown including a spherical protrusion engageable with the head to selectively adjust the angle.

17. A spinal implant system as recited in claim 16, further comprising a coupling member engageable with the inner surface to axially translate the crown into engagement with the head.

18. A spinal implant system as recited in claim 16, wherein the crown engages the head to rotate the bone screw shaft between a first orientation and a second orientation such that the bone screw shaft is locked with the receiver.

19. A spinal implant system as recited in claim 16, wherein the spinal rod is disposed with the saddle and the crown engages the head to rotate the bone screw shaft between a first orientation and a second orientation such that the spinal rod and the bone screw shaft are locked with the receiver.

20. A spinal implant system comprising:
    a plurality of alternate implant receivers including at least one implant receiver comprising an inner surface defining a groove and spaced apart arms that define an implant cavity therebetween, the at least one implant receiver including a crown being non-rotatable relative to the inner surface and a saddle movable relative to the crown;
    a bone screw shaft including a head engageable with an implant receiver such that the shaft is compatible with the plurality of implant receivers, the bone screw shaft being disposed at an angle relative to the at least one implant receiver; and a ring positioned in the groove such that the head extends through the ring to prevent downward axial translation of the bone screw shaft relative to the at least one implant receiver, wherein the at least one implant receiver is selected for connection with the shaft to comprise a bone fastener and the crown comprising a spherical protrusion engageable with the head to selectively adjust the angle.

\* \* \* \* \*

UNITED STATES PATENT AND TRADEMARK OFFICE
CERTIFICATE OF CORRECTION

PATENT NO. : 9,974,569 B2
APPLICATION NO. : 14/822425
DATED : May 22, 2018
INVENTOR(S) : Lehmann, Jr. et al.

Page 1 of 1

It is certified that error appears in the above-identified patent and that said Letters Patent is hereby corrected as shown below:

In the Specification

Column 5, Line 25, delete "dosed" and insert -- closed --, therefor.

Column 5, Line 29, delete "dosed," and insert -- closed, --, therefor.

Signed and Sealed this
Fourth Day of December, 2018

Andrei Iancu
*Director of the United States Patent and Trademark Office*